(12) United States Patent
Armstrong

(10) Patent No.: US 9,855,292 B2
(45) Date of Patent: Jan. 2, 2018

(54) CYANOCOBALAMIN, METHYLCOBALAMIN, AND/OR ADENOSYLCOBALAMIN TO HELP MAINTAIN A PAIN-FREE HEAD AND PAIN-FREE BODY AND PROVIDE DEFENSE AGAINST HEADACHES AND BODY PAIN

(71) Applicant: Ernest Timothy Armstrong, Palm Desert, CA (US)

(72) Inventor: Ernest Timothy Armstrong, Palm Desert, CA (US)

( * ) Notice: Subject to any disclaimer, the term of this patent is extended or adjusted under 35 U.S.C. 154(b) by 0 days.

(21) Appl. No.: 13/961,781

(22) Filed: Aug. 7, 2013

(65) Prior Publication Data

US 2015/0182548 A1    Jul. 2, 2015

(51) Int. Cl.
| | |
|---|---|
| *A61K 31/714* | (2006.01) |
| *A61K 9/00* | (2006.01) |
| *A61K 33/06* | (2006.01) |
| *A61K 31/205* | (2006.01) |
| *A61K 31/525* | (2006.01) |
| *A61K 31/122* | (2006.01) |

(52) U.S. Cl.
CPC .......... *A61K 31/714* (2013.01); *A61K 9/0056* (2013.01); *A61K 31/122* (2013.01); *A61K 31/205* (2013.01); *A61K 31/525* (2013.01); *A61K 33/06* (2013.01)

(58) Field of Classification Search
None
See application file for complete search history.

(56) References Cited

U.S. PATENT DOCUMENTS

| | | | | |
|---|---|---|---|---|
| 4,432,975 A * | 2/1984 | Libby | ..................... | A61K 33/14 514/52 |
| 5,925,625 A * | 7/1999 | Merkus | ................... | A61K 31/70 514/52 |
| 6,218,192 B1 * | 4/2001 | Altura | ..................... | A61K 31/28 424/677 |
| 6,255,294 B1 * | 7/2001 | Armstrong et al. | ............. | 514/52 |
| 8,652,463 B1 * | 2/2014 | Wilson | ................... | A61K 31/06 424/94.1 |
| 2008/0206360 A1 * | 8/2008 | Hendrix | ............... | A61K 31/375 424/682 |
| 2010/0291157 A1 * | 11/2010 | L'Europa | ............... | A61K 31/07 424/400 |

OTHER PUBLICATIONS

Ku, Min, et al. "Prevalence of migraine headaches in patients with allergic rhinitis." Annals of Allergy, Asthma & Immunology 97.2 (2006): 226-230.*
Sierpina, Victor, John Astin, and James Giordano. "Mind-body therapies for headache." Am Fam Physician 76.10 (2007): 1518-22.*
"Headaches". FamilyDoctor.org, Apr. 2014. Web Jun. 27, 2015 <http://familydoctor.org/famllydoctor/en/diseases-conditions/headaches>.*
Pringsheim, Tamara, et al. "Canadian Headache Society guideline for migraine prophylaxis." Can J Neurol. Sci 39.2 Suppl 2 (Mar. 2012): S1-S2.*
Sandor, P. S., et al. "Efficacy of coenzyme Q10 in migraine prophylaxis: a randomized controlled trial." Neurology 64.4 (2005): 713-715.*
Esfanjani, Ali Tarighat, et al. "The effects of magnesium, L-carnitine, and concurrent magnesium—L-carnitine supplementation in migraine prophylaxis." Biological trace element research 150.1-3 (Aug. 2012): 42-48.*
Press Release: "Cobalis Reports Phase III Trial Results for PreHistin in Seasonal Allergic Rhinitis." FierceBiotech.com (published Jul. 6, 2007).*
Press Release: "Cobalis to Commence Phase II Clinical Trials for Use of PreHistin(TM) to Prevent Atopic (Common) Migraine." PRNewsWire.com (published Jul. 26, 2004).*
Olesen, J., et al. The International Classification of Headache Disorders (ICHD-2). Cephalalgia 24, Suppl. 1 (2004): 1-151.*
Young, William B., Patricia Pozo-Rosich, and Mary F. Paolone. "Alternative therapies for headache." Current treatment options in neurology 5.6 (2003): 441-453.*
Dalsgaard-Nielsen, A. et al. Profylaktisk behandling of migraene med vitamin B12. Almindelige Danske Laegeforening 132:339-41 (1970).
Lauritzen M. Neuroimage 62(2):1040-50 (Aug. 15, 2012).
Van der Kuy, H. et al. Hydroxocobalamin, a nitric oxide scavenger, in the prophylaxis of migraine: an open, pilot study. Cephalalgia 22:513-519 (2002).
Xu, M. et al. Mitochondrial K(ATP) channel activation reduces anoxic injury by restoring mitochondrial membrane potential. Am. J. Physiol. Heart Circ. Physiol. 281(3):H1295-303 (Sep. 2001).
Zhuo, M. et al. KATP channel: relation with cell metabolism and role in the cardiovascular system. Int. J. Biochem. Cell Biol. 37 (4):751-64 (Apr. 2005).

* cited by examiner

*Primary Examiner* — Bethany Barham
*Assistant Examiner* — Peter Anthopolos
(74) *Attorney, Agent, or Firm* — Syndicated Law PC; Brian S. Boyer

(57) ABSTRACT

The current invention discloses novel approaches to help individuals defend against headaches and body pains with orally-delivered cyanocobalamin, methylcobalamin, adenosylcobalamin, and combinations thereof. Original clinical research conducted by the inventor on almost 2,000 humans yielded surprising and unexpected results showing differences in the frequency and severity of pains in the head and the body favoring cyanocobalamin patients over placebo. In one FDA-approved Phase III study on 1,551 patients, 4.4 percent of headaches and body pains were rated as "Severe" in the cyanocobalamin, group versus 11.5 percent in the placebo group. Once inside the body, cyanocobalamin is converted to methylcobalamin and adenosylcobalamin, but not to hydroxocobalamin. The current invention provides the patient's mitochondria with sufficient concentrations of essential micronutrients to survive, increase in number and manufacture the chemical energy (ATP) that is required to prevent the brief vasoconstriction followed by vasodilation associated with headache and body pain.

5 Claims, No Drawings

CYANOCOBALAMIN, METHYLCOBALAMIN, AND/OR ADENOSYLCOBALAMIN TO HELP MAINTAIN A PAIN-FREE HEAD AND PAIN-FREE BODY AND PROVIDE DEFENSE AGAINST HEADACHES AND BODY PAIN

CROSS REFERENCE TO RELATED APPLICATION

This application claims the priority right from the U.S. provisional patent application No. 61/695,540 that was filed on Aug. 31, 2012, the content of which is herewith incorporated in its entirety by reference.

FIELD OF THE INVENTION

The present invention generally relates to cyanocobalamin containing medications that are placed in the mouth, dissolved and swallowed for the prevention and treatment of headaches and body pains in humans and for enhancing the normal functioning of the human body by boosting the human defense against headaches and body pains.

BACKGROUND OF THE INVENTION

Human brains are one fiftieth of our body's weight, and yet consume up to one fifth of the body's energy. Two thirds of the brain's energy consumption goes into making nerve cells fire, and one third into cell maintenance. Most of the brain's energy is chemical energy manufactured in the mitochondria and stored in the form of ATP. Mitochondria live as organelles within cells, including brain cells. The number of mitochondria per cell can range from one to thousands, depending on the energy needs of the cell. Energy-hungry brain cells contain thousands of mitochondria. Once inside the body cyanocobalamin is converted to adenosylcobalamin and methylcobalamin. Adenosylcobalamin is critical to the health and functioning of the brain's mitochondria while methylcobalamin is critical to the health and functioning of the rest of the brain's and body's cells.

Muscle cells have a large energy demand and require lots of ATP. Muscle cells also have a correspondingly high number of mitochondria, and are often the site of the body's soreness and pain. The current invention focuses on musculoskeletal pain.

The current invention discloses novel approaches to prevent and treat the malfunctioning or underperformance of the body's mitochondria and cells with methylcobalamin, and adenosylcobalamin, and their chemical precursor, cyanocobalamin, especially in the central and peripheral nervous systems. The inventor of the current invention puts forth the theory that by providing cyanocobalamin, methylcobalamin, and/or adenosylcobalamin in therapeutic doses to headache and body pain sufferers that their mitochondria will attain sufficient therapeutic concentrations of these essential micronutrients to survive, increase in number and function properly, thereby not creating the symptoms of certain types of headache and body pain.

The current invention differs substantially from prior uses of cobalamins, such as hydroxycobalamin to take up excess nitric oxide, or cobalamins to prevent IgE-mediated allergic diseases, neurogenic inflammation or cobalamins to repair nerve cell-insulating myelin sheath.

Cyanocobalamin, methylcobalamin, adenosylcobalamin and hydroxocobalamin each contain a biologically rare cobalt metal atom as a central feature. Around that cobalt is the active part of each molecule (i.e. the moiety) which is the location responsible for the unique type of chemical reactions that molecule causes to make happen. Attached to their central cobalt atoms; cyanocobalamin has a cyano group, methylcobalamin has a methyl group, adenosylcobalamin has an adeno group, and hydroxocobalamin has a hydroxyl (OH) group. Because of these distinct electromagnetic properties, each of these compounds plays a distinct biochemical role.

Cyanocobalamin, methylcobalamin, and adenosylcobalamin (the three chemicals pertaining to the current patent) differ in some important ways from hydroxocobalamin (which does not pertain to the current patent).

Once inside the body cyanocobalamin is converted to methylcobalamin and adenosylcobalamin, but not to hydroxocobalamin.

Hydroxocobalamin is known to scavenge nitric oxide (NO) which is associated with migraine. Hydroxocobalamin does this scavenging by trading its OH group connected to its central cobalt with the nitric oxide molecule. Because neither cyanocobalamin, nor methylcobalamin, nor adenosylcobalamin have the ability to scavenge nitric oxide, their ability to lessen the frequency and severity of headaches cannot be ascribed to nitric oxide scavenging.

In 1999 Merkus disclosed in U.S. Pat. No. 5,925,625 a method and composition for the prophylaxis and treatment of headaches using intranasal hydroxocobalamin. The current invention can be distinguished from Merkus' patent because the current invention discloses the use of different chemical entities, namely cyanocobalamin, methylcobalamin, and adenosylcobalamin. The current invention can be distinguished from Merkus' patent because Merkus describes a short-term treatment while the current patent describes a long-term treatment. The current invention can be further distinguished from U.S. Pat. No. 5,925,625 because Merkus states that "Oral, sublingual as well as nasal administration of vitamin B12 appeared to be ineffective treatments . . . " while the current patent teaches away from Merkus because the current patent discloses that buccal and sublingual administration do indeed yield effective treatments for headache.

In 2001 Ernest T. Armstrong (the inventor of the current invention) disclosed in U.S. Pat. No. 6,255,294 a method to treat allergy using cobalamins. However, in U.S. Pat. No. 6,255,294 there is no mention of headache or migraine. In U.S. Pat. No. 6,255,294 the invention relied on a method for treating Immunoglobulin E (IgE) mediated atopic disease including allergic rhinitis and asthma. Such atopic diseases are a completely different class of disease and human condition with different causations and modes of action than the headaches and body pains disclosed in the current invention. The claims of U.S. Pat. No. 6,255,294 were approved with cyanocobalamin, methylcobalamin, and hydroxocobalamin, but not with adenosylcobalamin.

In 2002 van der Kuy showed in an unblinded, open-label study on 19 migraine patients that intranasal hydroxocobalamin can have an effect on migraine. The authors of the van der Kuy study hypothesize that hydroxocobalamin might be effective in migraine because of its nitric oxide-scavenging activity. Flaws in the van der Kuy study include the lack of a placebo group as a comparator, and the lack of any follow up after the last day the subjects received their last dose of medication which could have demonstrated (or not demonstrated) a persistence of effect. The current invention can be distinguished from van der Kuy's research because van der Kuy used hydroxocobalamin while the current invention discloses the distinct chemical entities of cyanocobalamin, methylcobalamin, and adenosylcobalamin. The current invention can be distinguished from van der Kuy's research because van der Kuy's treatment has a short-term persistence of effect while the current invention has a long-term effect. The current invention can be distinguished from van der Kuy's research because for all subjects van der Kuy showed essentially no reduction in severity (mean of 2.2 at baseline versus 2.1 at the end of the study, on a 0-3 scale). The current invention can be further distinguished from van der Kuy's research because van der Kuy's mechanism of action describes hydroxocobalamin as a nitric oxide (NO) scavenger. Nitric oxide is created and excreted by the body within a matter of hours. The important distinguishing point is that the current invention's mechanism of action most certainly is different than that of van der Kuy's invention because the scavenging of nitric oxide lasts only hours while the current invention has a persistence of effect lasts weeks, and perhaps months or years. (Van der Kuy, H et al. Hydroxocobalamin, a nitric oxide scavenger, in the prophylaxis of migraine: an open, pilot study. Cephalalgia, 2002, 22, 513-519.)

Dalsgaard-Nielsen performed a double-blind, placebo-controlled study on 29 patients (active n=15 and placebo n=14). During two months every two weeks 2 mg of cyanocobalamin were administered intramuscularly. The patients reported a: "Good result" active n=4 versus placebo n=2, and "Considerable improvement" active n=2 versus placebo n=5. The authors concluded that no therapeutic effect attributable to cyanocobalamin was demonstrated. (Dalsgaard-Nielsen A T, Trautmann J. Profylaktisk behandling af migraene med vitamin B12. Almindelige Danske Laegeforening 1970; 132:339-41.)

The authors of the van der Kuy study also hypothesize that since cyanocobalamin has no nitric oxide-scavenging activity, in contrast to hydroxocobalamin, it is not surprising that in the Dalsgaard-Nielsen trials on cyanocobalamin no effect was seen in migraine patients. Van der Kuy was correct about the lack of cyanocobalamin's nitric oxide-scavenging activity, but they missed another flaw in the Dalsgaard-Nielsen trials: Dalsgaard-Nielsen administered cyanocobalamin only once every two weeks. Based on the current inventor's original clinical research, the current invention teaches away from Dalsgaard-Nielsen and discloses a particularly preferred embodiment of daily administration of cyanocobalamin, with repeated delivery ranging from about 15 days to about 60 days.

The non-obviousness of the instant claims can be established by considering that oral (buccal) dissolving strip, sublingual lozenges and other disclosed means of introducing the headache and body pain opposing medications orally provide significant improvements over the prior art in that the dissolving strip are more convenient for the headache patient than a series of injections, or a nasal spray. Compared to an injection, or nasal spray, a dissolving strip or a sublingual lozenge is much more convenient because it takes from between one minute and five minutes to inject oneself or to administer a nasal spray. These few minutes may not seem like much, but to the headache patient, time is of the essence.

Another advantage is that people in pain do not want something stuffed up their nose or an injection in the body.

Among the surprising advantages of the dissolving strip and sublingual lozenge over the injection and nasal spray is that the headache patient would not be further irritated by a painful injection process or by a nasal spray up a sensitive nostril. This is an important aspect of the oral strip which comes in an easy to use soft plastic container because headache patients are often hypersensitive to bright lights (photophobia), shrill sounds (phonophobia), smells (osmophobia), and metallic objects touching the body. Such extraneous irritations are the last thing a headache sufferer would want at the time he or she is experiencing an episode of headache, thus the strips and sublingual lozenge differ in a significant way.

The significance of the difference between the oral dissolving medication and other delivery means becomes apparent when one examines the large numbers of people and money involved. There are between 30 and 50 million headache sufferers in the United States, thus if only ten percent can be provided an improvement, then some 3 to 5 million people will be helped. According the American Academy of Pain Medicine, pain affects more Americans than does diabetes, heart disease, and cancer combined. Back pain problems in the United States are reported to cost more than $100,000,000,000 annually.

Many large pharmaceutical companies have spent millions of dollars over many years investigating new medications for headache sufferers, but none of them have developed any medication with the safety profile, efficacy and ease of use afforded by the current invention.

EXAMPLE 1

This clinical study was designed and directed by the inventor of the current patent. Methods: 162 human subjects with demonstrated seasonal allergic rhinitis (hay fever) in the Pacific Northwest region of the United States were split into two groups with approximately 50 percent in the active group and 50 percent in the placebo group. Subjects were given their study medication, either Cyanocobalamin, USP or placebo in the a.m. and p.m. every day for 21 consecutive days. Data on adverse events including headache was captured throughout the ten-week duration of the study. Week One was a baseline during which time no medication was administered; Weeks Two, Three and Four were the weeks during which time the subjects received their study medication; and Weeks Five through Ten were a post-treatment period during which time no medication was administered but observations of symptoms and adverse events were documented. Each time a subject felt a "Headache", he or she reported its occurrence.

Results: The subjects' post-treatment reports of "Headache" decreased from baseline in the following surprising and unexpected results: Week Five −1.4 active vs. −0.9 placebo, Week Six −1.6 active vs. −2.0 placebo, Week Seven −1.4 active vs. −0.1 placebo, Week Eight −2.1 active vs. −1.2 placebo, Week Nine −3.4 active vs. −1.8 placebo, and Week Ten −3.2 active vs. −0.3 placebo.

The results also demonstrated a persistence of effect of at least six weeks after finishing the treatment. The results also demonstrated that there was a greater reduction in the frequency of headache in the active group versus placebo in five out of six post-treatment weeks. Additionally, almost one year later a follow-up questionnaire was completed by 43 active and 49 placebo subjects, the results of which suggest a persistence of effect lasting almost one year.

EXAMPLE 2

This clinical study was designed and directed by the inventor of the current patent. A large, multi-center, Phase 3, randomized, placebo-controlled clinical study on 1,551 patients was designed and directed by the inventor of the current patent. Methods: The study was titled: "A Phase 3, randomized, double-blind, placebo-controlled, parallel group study of the safety and efficacy of pre-seasonal sublingual cyanocobalamin lozenges on moderate to moderately severe seasonal allergic rhinitis in humans". The study took place before and during the ragweed pollen season at 23 study sites in the Midwest, Northeast and Central Texas regions of the United States. Essentially all of the 23 investigators were Board Certified in Allergy/Immunology. Qualified subjects were randomized into an active or placebo group (approximately 50% and 50%) using an interactive voice recognition system (IVRS). All subjects (or their guardians) signed an Informed Consent form approved by the IRB. Each subject had three visits to the clinic. At Visit 1 and at Visit 3, they were given a physical exam (HEENT, chest, lungs, heart, vital signs, height and weight); and donated blood and urine samples for laboratory analysis. CBC and chemistry panels were run for safety analyses. The blood samples were analyzed by chemiluminescent immunoassay for the presence of ragweed specific immunoglobulin epsilon (IgE), and were assayed for cobalamins (cyanocobalamin, methylcobalamin and adenosylcobalamin) levels.

Subjects self-rated the severity their allergy symptoms in the morning (a.m.) and in the evening (p.m.) by entering a numeric score in a keypad of a telephone (IVRS) or in a computer connected via the Internet to a database.

Subjects were given their study medication, either 3.3 mg Cyanocobalamin, USP or placebo in the a.m. and p.m. Subjects were instructed to let the study drug "dissolve completely in your mouth, especially under your tongue, then swallow.". Subjects self-administered the study medications for six consecutive weeks. For the next four weeks subjects did not take any study medications.

Any adverse event (AE) or serious adverse event (SAE) was documented by the subject in a paper diary and then transcribed to the appropriate case report form (CRF) page. All SAEs were attended to by the investigator, and reported to the FDA by the sponsor. All sites were monitored multiple times by qualified monitors.

Results: There was a total enrollment of 1,551 subjects (RA5555 n=763 and RA3333 n=788). The total number of doses possible was 84 doses. Over 50 percent (n=766) of the 1474 subjects who reported taking at least one dose, took at least 80 doses of study medication.

The allergy symptom scores were derived by summing and averaging all a.m. plus all p.m. scores for the symptoms of sneezing, runny nose, nasal congestion, nasal itch and eye itch. The primary comparison of interest was the scores across Weeks 4, 5 and 6 (i.e. during the pollen season). All randomized subjects who took at least one dose were included in this intent-to-treat (ITT) analysis. The reduction in symptom severity from baseline was greater for the active group than the placebo group for all five composite symptoms: sneezing, runny nose, nasal congestion, nasal itch and eye itch.

In terms of safety, the active study medication was well tolerated.

As per the laboratory results, a significant average increase of more than 250 percent in post-treatment blood serum cobalamin (cyanocobalamin, methylcobalamin and adenosylcobalamin) levels was reported in the cyanocobalamin-treated subject groups compared with essentially no increase in placebo-treated subjects.

The following types of headaches were self-diagnosed and documented by subjects in the study: tension headache, headache, migraine, increased frequency of headaches, worsening sinus migraine headache, increased headache, headache worsening, worsening of migraine, sinus headache, severe sinus headache, and sinus pressure headache.

The following types of body pains and myasthenia were self-diagnosed and documented by subjects in the study: ear pain, earache, sore throat, sore muscles, leg cramps, myalgia, back pain, sprained ankle, ache, toothache, hip pain, finger pain, knee pain, pulled back muscle, shoulder pain, pulled hamstring, neck pain, femur pain, gum pain, sore muscle, toenail pain, sore foot, and pulled neck muscle.

Of the 294 documented reports of some type of headache and of body pain, the study yielded the following surprising and unexpected frequencies demonstrating positive results: 137 reports in the active group compared to 157 reports in the placebo group. The severities of those headaches and body pains were rated in the following surprising and unexpected intensities: "Mild" 63 reports (or 46.0%) in the active group versus 71 reports (or 45.2%) in the placebo group; "Moderate" 68 reports (or 49.6%) in the active group versus 68 reports (or 43.3%) in the placebo group; and "Severe" 6 reports (or 4.4%) in the active group versus 18 reports (or 11.5%) in the placebo group.

EXAMPLE 3

The current invention was successfully tested in humans with a history of headache and/or body pains in a variety of formulas. These formulas comprised dissolving medications containing combinations of cyanocobalamin, methylcobalamin, adenosylcobalamin, magnesium, coenzyme Q10, L-carnitine, and riboflavin.

Formula 1 was a dissolving medication with 3.3 mg of cyanocobalamin.

Formula 2 was a dissolving medication with 6.6 mg of cyanocobalamin.

Formula 3 was a dissolving medication with 3.3 mg of methylcobalamin.

Formula 4 was a dissolving medication with 3.3 mg of adenosylcobalamin.

Formula 5 was a dissolving medication with 2.2 mg of cyanocobalamin, 2.2 mg of methylcobalamin, and 2.2 mg of adenosylcobalamin.

Formula 6 was a dissolving medication with 3.3 mg of adenosylcobalamin.

Formula 7 was a dissolving medication with 5.6 mg of cyanocobalamin, 0.5 mg of methylcobalamin, and 0.5 mg of adenosylcobalamin.

Formula 8 was a dissolving medication with 1.1 mg of cyanocobalamin, 1.1 mg of methylcobalamin, and 1.1 mg of adenosylcobalamin.

Formula 9 was a dissolving medication with 2.2 mg of cyanocobalamin, 2.2 mg of methylcobalamin, 2.2 mg of adenosylcobalamin, 15 mg of coenzyme Q10, and 2.1 mg of riboflavin.

Formula 10 was a dissolving medication with 1.1 mg of cyanocobalamin, 1.1 mg of methylcobalamin, 1.1 mg of adenosylcobalamin, 18 mg of coenzyme Q10, and 2.1 mg of riboflavin.

Formula 11 was a dissolving medication with 1.1 mg of cyanocobalamin, 1.1 mg of methylcobalamin, 1.1 mg of adenosylcobalamin, 5 mg magnesium, 9 mg of coenzyme Q10, 5 mg L-carnitine, and 2.1 mg of riboflavin.

Formula 12 was a dissolving medication with 5.6 mg of cyanocobalamin, 0.5 mg of methylcobalamin, 0.5 mg of adenosylcobalamin, 15 mg of coenzyme Q10, and 1 mg of riboflavin.

Formula 13 was a dissolving medication with 5.6 mg of cyanocobalamin, 0.5 mg of methylcobalamin, 0.5 mg of adenosylcobalamin, 5 mg magnesium, 10 mg of coenzyme Q10, and 2.1 mg of riboflavin.

Formula 14 was a dissolving medication with 5.6 mg of cyanocobalamin, 0.5 mg of methylcobalamin, 0.5 mg of adenosylcobalamin, 10 mg of coenzyme Q10, and 1 mg of riboflavin.

DETAILED DESCRIPTION OF THE PREFERRED EMBODIMENTS

Headaches, such as tension headache and sinus headache, are painful and can rob individuals of quality of life. Headache symptoms include a pounding headache, nausea, vomiting, and light sensitivity. Body soreness is a pain in the body. Conventional headache and body pain remedies include various types of pain relievers, pain killers, and analgesics, including COX-1, COX-2, opioids, and NSAIDs; none are without side-effects, including drug addiction, liver damage and cardiovascular events; and none get to the truly underlying causes of pain and neurological health, as does the current invention.

The International Classification of Headache Disorders (ICHD) is a classification of headaches published by the International Headache Society. The current patent applies to primary headaches which the ICHD-2 classification defines as migraines, tension-type headaches, cluster headache and other trigeminal autonomic cephalalgias stabbing headaches, headaches due to cough, exertion and sexual activity (coital cephalalgia), continuous headache on one side of the head (hemicrania continua), paroxysmal hemicrania, daily-persistent headaches along with the hypnic headache and thunderclap headaches.

Vitamin B12 or simply B12 are unspecific terms often used casually for a variety of cobalamins, including cyanocobalamin, methylcobalamin, and adenosylcobalamin.

All other headache remedies with adequate research proving their efficacy have safety profiles that contrast sharply with cyanocobalamin, methylcobalamin, and adenosylcobalamin which are considered by the nutritionists and the FDA to have excellent safety profiles, they are so safe and vital to health, that—like exceedingly few other products—they are recommended to women who are pregnant and lactating! The metal cobalt plays a central role in these molecules with its unique electrochemical bounding abilities. These molecules are the only molecules in the human body to utilize these special properties of cobalt, are difficult to absorb from food, and cannot be manufactured by the body.

Cyanocobalamin (also known as CNCbI, or 5,6-dimethylbenzimidazolyl cyanocobamide) has the molecular formula $C_{63}H_{88}CoN_{14}O_{14}P$. Cyanocobalamin is a manufactured commercial form of a cobalamin, and not native to the human body. Once inside the body cyanocobalamin is converted to methylcobalamin and adenosylcobalamin, but not to hydroxocobalamin.

Methylcobalamin (also known as mecobalamin, or MeCbl) has the molecular formula $C_{63}H_{91}CoN_{13}O_{14}P$ and is notable as a rare example of an enzyme that contains metal-alkyl bonds. Methylation is the donation of a methyl group to a substrate, and methylcobalamin can function as the donor molecule. Proper DNA replication and cell division require methylation. For this reason, and others, the current invention includes cyanocobalamin and methylcobalamin.

Adenosylcobalamin (also known as cobamamide, AdCbl, or dibencozide) comprises more than 70 percent of the cobalamins in the brain. Adenosylcobalamin functions in reactions in which hydrogen groups and organic groups exchange places. Adenosylcobalamin is the major form in cellular tissues, especially energy-hungry muscles, where it is retained in the mitochondria. Adenosylcobalamin is the coenzyme for the mitochondrial enzyme methylmalonyl CoA mutase. Problems with methylmalonyl CoA mutase can lead to methylmalonic aciduria and dysfunction of the mitochondria. In one preferred embodiment of the current invention, adenosylcobalamin is included to prevent dysfunction of the mitochondria in the brain.

The mitochondrion (plural mitochondria) is the "cell's powerhouse". Most of the organism's stored energy is converted into a usable chemical energy known as adenosine triphosphate (ATP) in the mitochondria. The citric acid cycle or Krebs cycle generates GTP which becomes ATP. Problems with the mitochondria can cause them to die. Problems with the mitochondria, which are also involved in cell signaling, cell death, and cell differentiation, can disrupt the functioning of the cell, tissue and organ in which they survive. It is an organelle with its own strand of DNA, distinct from DNA in the nucleus. Mitochondria are found inside most animal cells. Populations of mitochondria per cell range from one to thousands. Mitochondria living in our cells may be hitch-hiking, symbiotic descendants of bacteria that provided some benefits to us, indeed mitochondrial DNA resembles bacterial DNA. We certainly provided a safe living cell as home with all the warmth and nutrients to these bacteria. When one realizes that the basic chemical structure of cobalamins can only be synthesized by bacteria, it is not hard to see a critical connection and history between mitochondria and cobalamins.

Consistent with the idea that certain types of headache are a result of insufficient energy production by the mitochondria are reports of headache remedies that lessen the brain's demand for energy including relaxation techniques, meditation, and calming affirmations while hypnotized. Also consistent are reports that providing more oxygen to an individual can ameliorate headaches, such treatments include repeated deep breathing and hyperbaric oxygen. Other consistent findings are that regular exercise can both prevent headaches and that exercise can increase the number of mitochondria in the brain. Conversely, strenuous physical activity by people who are not accustomed to it can reduce oxygen concentrations in the brain and have been reported to trigger a benign exertion headache. Likewise carbon monoxide (which binds up hemoglobin) and tobacco smoke can reduce oxygen and are associated with headache. Brain scans called fMRI detect where there is increased blood flow in the brain, which is a surrogate indicator for where there is increased brain activity. Such fMRI scans show that three of the highest energy demanding functional areas of our brains are those areas which process vision, smell and hearing. Accordingly the mitochondrial dysfunction theory of headache is consistent with the hypersensitivity of headache sufferers to bright lights, bad smells, and loud noises. Indeed, visual disturbances known as aura can occur an hour or so prior to the onset of a headache.

The brain's electrical activity correlates to changes in cerebral blood flow and cerebral metabolic rate of oxygen. Rises in cerebral metabolic rate of oxygen are controlled by the ATP turnover, which depends on the energy used for the Na, K-ATPase to re-establish ionic gradients, while cerebral blood flow responses are controlled by mechanisms that depend on $Ca(2+)$ rises in neurons. (Lauritzen M, Neuroimage, 2012 Aug. 15; 62(62(2):1040-50.) Caffeine acts as a stimulant because it constricts the brain's blood vessels and many analgesics contain caffeine to fight headaches, especially vascular headaches including migraines. Other products, such as adenosine, have the opposite effect because they dilate blood vessels in the brain and the increased blood flow can lead to a headache. Vasodilation may be part of a headache, yet it is not required for migraine symptoms to manifest. Vasodilation and the brief vasoconstriction that generally precedes it are not the root causes of vascular headaches, as once believed.

The current invention teaches away from the prior art in its findings. The seemingly contradictory idea that headaches are caused by insufficient metabolism of oxygen in the mitochondria, and that increasing blood flow is also a cause of headaches can be reconciled as follows: Blood vessels over essentially all of the brain are normally constricted in a resting, non-headache state, and it is only at the local functional area(s) in the brain where current neurological processing is taking place that momentary vasodilation of the blood vessels (i.e. increases in local cerebral blood flow) occur. (This increased local blood flow can be seen in fMRI images that detect the iron in hemoglobin being fed to the high activity locations.) This local spike in cerebral blood flow delivers a quick, just-in-time oxygen supply to permit a local increase in the cerebral metabolic rate of oxygen. Ameliorating headaches by restricting blood flow all over the brain (increasing mean arterial pressure) is analogous to keeping all the fire hydrants in a city sealed shut except that one hydrant in front of a burning building where opening just that one hydrant provides sufficient pressure to blast the water out.

Hours or days prior to the onset (aura) of a migraine attack, a headache sufferer often experiences a set of symptoms known as prodrome consistent with the current invention's teachings of mitochondrial dysfunction or underperformance in the brain and muscles. Prodrome's symptoms include mood changes, muscle stiffness, yawning (which is a call for more oxygen), fatigue and food (nutrition) cravings.

The current inventor contends that the root cause of many headaches and body pains is inadequate energy (ATP) production in the mitochondria needed to fuel the energy-hungry brain and muscle cells (and not the inflammatory response as per conventional wisdom), and that surprisingly the current invention can provide the micronutrients needed as raw materials to permit the optional functioning of mitochondria.

A non-obvious mechanism of action disclosed in the current invention is that increased mitochondrial concentrations of adenosylcobalamin (and also coenzyme Q10, magnesium, L-carnitine, and riboflavin) prevent or lessen the severity of a cellular energy crisis in which mitochondrial function declines. Such a decline can be due to alternating inner membrane potential, imbalanced trans-membrane ion-transport, and an overproduction of free radicals. (Zhuo M L, Huang Y, Liu D P, Liang C C (April 2005). "KATP channel: relation with cell metabolism and role in the cardiovascular system". Int. *J. Biochem. Cell Biol.* 37 (4): 751-64.) In such a situation, mitochondrial K(ATP) channels open and close to regulate both internal Ca2+ concentration and the degree of membrane swelling. This helps restore proper membrane potential, allowing further H+ outflow, which continues to provide the proton gradient necessary for mitochondrial ATP synthesis. Without aid from the potassium channels, the depletion of high energy phosphate would outpace the rate at which ATP could be created against an unfavorable electrochemical gradient. (Xu M, Wang Y, Ayub A, Ashraf M (September 2001). "Mitochondrial K(ATP) channel activation reduces anoxic injury by restoring mitochondrial membrane potential". *Am. J. Physiol. Heart Circ. Physiol.* 281 (3): H1295-303.)

An ATP-sensitive potassium channel is a type of potassium channel that is gated by ATP. Simply stated, levels of ATP influence constriction and dilation of blood vessels which have receptors for ATP known as P2x-R. Many vascular headaches, including migraine, begin with a brief vasoconstriction immediately followed by vasodilation, resulting in a throbbing headache. The current invention therefore surprisingly prevents headaches by providing the micronutrients needed for the mitochondria to function properly.

Any shortage or deficiency of adenosylcobalamin and/or the other micronutrients disclosed in the current invention will impair or inhibit mitochondrial functioning. Additionally, increasing amounts of adenosylcobalamin and/or the other micronutrients disclosed herein will accelerate the chemical reactions in the mitochondria, thereby permitting the mitochondria to metabolize more chemical energy over a given period of time.

One example of the utility of the current invention is its amelioration of mitochondrial dysfunction in the hypothalamus, a hormone secreting region of the brain which is associated with cluster headaches.

One especially preferred embodiment of the current invention is a once-daily dissolving that is placed on the tongue and swallowed, and contains combinations of cyanocobalamin, methylcobalamin, and adenosylcobalamin in amounts that are effective in defending the individual against headache and body pain; and the current invention also includes one or more of the following substances or metabolites and salts thereof: magnesium, coenzyme Q10, L-carnitine, and riboflavin.

Magnesium ions are important to the production of nucleic acid, DNA, and RNA, and the catalytic action of many enzymes. Of special relevance to the current invention are the magnesium-dependant enzymes associated with the conversion of adenosine triphosphate (ATP) into adenosine diphosphate (ADP) in the mitochondria. Phosporylation is an important process that occurs in the mitochondria. For this reason, one particularly preferred embodiment of the current invention includes elemental magnesium, magnesium oxide, magnesium gluconate, magnesium citrate, magnesium oxide, magnesium orotate, magnesium malate, and combinations thereof in the formulation in amounts ranging from about 10 mg to about 500 mg per portion.

Proper functioning of the mitochondria requires coenzyme Q10 (CoQ10), also known as ubiquinone or 1-4-benzoquinone. In one preferred embodiment, coenzyme Q10 is included in the formulation in amounts ranging from about 10 mg to about 500 mg per portion.

Riboflavin (vitamin B2) has an important function in energy metabolism. Flavin mononucleotide (FMN) and flavin adenine dinucleotide (FAD) function as coenzymes for a wide variety of oxidative enzymes and remain bound to the enzymes during the oxidation-reduction reactions. Reduction of isoalloxazine ring (FAD, FMN oxidized form) yields the reduced forms of the flavoproteins (FMNH2 and FADH2). For this reason, one particularly preferred embodiment of the current invention includes riboflavin in the formulation in amounts ranging from about 0.1 mg to about 300 mg per portion.

Levocarnitine (or L-carnitine) plays an important role in energy metabolism by helping the transport of fatty acids from the cytosol into the mitochondria. Also, it helps remove toxic chemical byproducts from the mitochondria so they do not accumulate. In one preferred embodiment of the current invention, L-carnitine, acetyl-L-carnitine (L-acetylcarnitine), L-propionyl carnitine, or L-carnitine fumarate, and combinations thereof is included in doses between 1 mg and 400 mg per portion.

One especially preferred embodiment of the current invention is a once-daily dissolving medication that is placed on the tongue and swallowed, and contains combinations of cyanocobalamin, methylcobalamin, adenosylcobalamin, magnesium, coenzyme Q10, and riboflavin in amounts that are effective in defending the individual against headache and body pain.

One particularly preferred embodiment of the current invention is a once- or twice-daily dissolving that is placed on the tongue and swallowed. Each dosage's approximate contains are: 1.1 mg of cyanocobalamin, 1.1 mg of methylcobalamin, 1.1 mg of adenosylcobalamin, 5 mg of coenzyme Q10, and 1.2 mg of riboflavin.

In one preferred embodiment, the current invention includes one or more of the following plants or extracts thereof: feverfew (*Tanacetum parthenium, Chrysanthemum parthenium, Pyrethrum parthenium*), kudzu (*Pueraria lobata*), capsicum (*solanaceae*), butterbur (*Petasites hybridus*), ginger (*zingiber officinale*) and ginko (*ginko biloba*).

In the current invention, formulation of dissolving medication can employ hydrophilic polymers that rapidly dissolve in the mouth, preferably on top of the tongue. The cyanocobalamin, methylcobalamin, and adenosylcobalamin permeate the skin of the mouth and, in a certain percentage, are ingested for absorption by the gut, especially the ileum. In one preferred embodiment of the current invention, formulation of dissolving medication involves the application of both aesthetic and performance characteristics such as polymers, plasticizers, active pharmaceutical ingredients, sweetening agents, saliva stimulating agents, flavoring agents, coloring agents, stabilizing and thickening agents. In the current invention, formulation of dissolving medication can employ polymers such as maltodextrin, microcrystalline cellulose and piroxicam made with a hot extrusion technique. To make the medication more flexible; plasticizer excipients such as propylene glycol, glycerol, dimethyl phthalate, diethyl phthalate, dibutyl phthalate, triacrtin, castor oil, triethyl citrate, tributyl citrate, acetyl citrate in the current invention. In one preferred embodiment of the current invention Stevia (steviol glycoside) is used to sweeten the medications.

In one particularly preferred embodiment, the headache medication is delivered to the headache sufferer in a dissolving medication placed in the mouth. The dissolving medication is a thin film delivery technology, and is also referred to as a dissolving film or an oral strip. The current invention defines a dissolving strip as a thin film delivery means to administer active agent(s) via absorption in the mouth. This absorption can be in the mouth as a whole (buccally) on top of the tongue (supralingually), or under the tongue (sublingually) followed up by swallowing.

The skin, including the surface of the tongue, provides a physical barrier that can interfere with the absorption of active drug ingredients. Although cyanocobalamin, methylcobalamin, and adenosylcobalamin are known to permeate the skin in the mouth, a penetration enhancer can increase their transdermal delivery in one preferred embodiment. Penetration enhancers that can increase transdermal delivery and can be used preferably in various embodiments of the current invention include but are not limited to: dimethyl isosorbide, alpha bisobola, sulphoxides (e.g. dimethylsulphoxide), azones (e.g. laurocapram), pyrrolidones (e.g. 2-pyrrolidone), alcohols and alkanols (e.g. ethanol and decanol), glycols (e.g. propylene glycol), surfactants, terpenes, fatty acids, fatty acid esters, fatty alcohols, fatty alcohol esters, biologics, enzymes, amines, amides, complexing agents, macrocyclics, classical surfactants and the like. Gels and creams with a Lamellar or liquid crystal structure also enhance penetration of active ingredients.

When considering the various embodiments of the invention described herein, those knowledgeable in the art will appreciate that these are illustrative only. Such embodiments do not limit the scope of the invention. Those knowledgeable in the art involved will appreciate that many variations, substitutions, equivalents, and like modifications may be made within the scope of the present invention.

SUMMARY OF THE INVENTION

Consistent with original study findings on almost 2,000 people, most of whom were in a Phase III placebo-controlled clinical study, the present invention is directed to safe and effective cyanocobalamin, methylcobalamin, and/or adenosylcobalamin containing, orally-dissolving medications to reduce the frequency and severity of pains in the head and body in humans and for enhancing the normal functioning of the human body by boosting the human defense against headaches and body pains.

A non-obvious mechanism of action disclosed in the current invention is that higher concentrations of adenosylcobalamin (and other disclosed compounds) in the mitochondria prevent or lessen the severity of a cellular energy crisis in which mitochondrial function declines. Mitochondria convert sugars into chemical energy the cell can use called ATP. Levels of ATP also function to constrict and dilate blood vessels. Many vascular headaches, including migraine, begin with a brief narrowing of the blood vessels (vasoconstriction) followed by an opening up blood vessels resulting in a throbbing headache. The current invention therefore surprisingly prevents headaches by providing the micronutrients needed for the mitochondria to function properly.

What I claim is:

1. A method of treating or preventing headache in a human in need thereof, comprising orally administering a dissolvable medicament, wherein the medicament comprises a compound selected from the group consisting of cyanocobalamin, methylcobalamin, adenosylcobalamin, or combinations thereof; said headache being selected from the following classes of headaches: tension-type, stabbing, cough, exertion, coital cephalalgia, hemicrania continua, daily-persistent, hypnic, and thunderclap.

2. The method of claim 1, wherein said medicament is in the form of a dissolving strip, a lozenge, a spray, a tablet, a capsule, a dot, a solution, an emulsion, an encapsulated microsphere, or a suspension.

3. The method of claim 1, wherein said medicament is administered on top of the tongue, under the tongue, or combinations thereof.

4. The method of claim 1, wherein said medicament comprises 0.05 mg to 6 mg cyanocobalamin, and/or 0.05 mg to 6 mg methylcobalamin, and/or 0.05 mg to 6 mg adenosylcobalamin.

5. The method of claim 1, wherein the medicament further comprises at least one compound selected from the group consisting of L-carnitine, coenzyme Q10, riboflavin, caffeine, melatonin, L-arginine, feverfew, kudzu, capsicum, butterbur, ginger, and/or ginkgo.

* * * * *